(12) United States Patent
Hillsman

(10) Patent No.: US 6,273,088 B1
(45) Date of Patent: Aug. 14, 2001

(54) VENTILATOR BIOFEEDBACK FOR WEANING AND ASSISTANCE

(75) Inventor: Deane Hillsman, Sacramento, CA (US)

(73) Assignee: Sierra Biotechnology Company LC, McLean, VA (US)

( * ) Notice: Subject to any disclaimer, the term of this patent is extended or adjusted under 35 U.S.C. 154(b) by 0 days.

(21) Appl. No.: 09/093,021

(22) Filed: Jun. 8, 1998

Related U.S. Application Data

(60) Provisional application No. 60/049,573, filed on Jun. 13, 1997.

(51) Int. Cl.[7] .................................................... A61M 16/00
(52) U.S. Cl. .............................. 128/204.23; 128/204.18
(58) Field of Search ........................... 128/204.23, 204.18

(56) References Cited

U.S. PATENT DOCUMENTS

| | | | | |
|---|---|---|---|---|
| 3,991,304 | * | 11/1976 | Hillsman | 235/151.34 |
| 4,984,158 | * | 1/1991 | Hillsman | 364/413.04 |
| 5,582,182 | * | 12/1996 | Hillsman | 128/716 |

OTHER PUBLICATIONS

A Visual Biofeedback Method to Define and Teach Breathing Patterns–Hillsman, Deane—Biological Psychology, v. 43, Issue 3—Jun. 28, 1996—p. 261.*
Clinical Experience with a Visual Biofeedback Method in COPD Rehabilitation–Hillsman, Deane—Biological Psychology, v 43, Issue 3, Jun. 28, 1996—pp. 243–244.*
The Reduction of Weaning Time from Mechanical Ventilation Using Tidal Volume and Relaxation Biofeedback—Holliday, Jerome E. & Hyers, Thomas M—American Review of Respiratory Diseases—1990—v. 141—pp. 1214–1220.*

* cited by examiner

Primary Examiner—John G. Weiss
Assistant Examiner—Mital B. Patel

(57) ABSTRACT

Apparatus and method to monitor patient breathing during weaning from ventilator dependency to assure adequate performance and safety, and to provide visual respiratory biofeedback breathing patterns to prompt respiratory center neurologic signals to normal performance.

The device permits setting desired breathing patterns within an optimal level of ventilation, and to establish and monitor a level of lowest permissible ventilation to define minimum safe levels of ventilation, and to permit definition of patient exhaustion and therefore need to terminate the weaning trial.

The device may be used in weaning trials of spontaneous breathing, or in conjunction with ventilator assistive modes of all types. Used in conjunction with a plurality of ventilators the device may signal the ventilator to assist if the patient's attempts to breathe fall below predetermined safe levels of ventilation. The device may also be used to prompt patients in acute respiratory failure in correct breathing patterns for proper use of non-invasive ventilator assistance in order to prevent the need for invasive intubation.

11 Claims, 6 Drawing Sheets

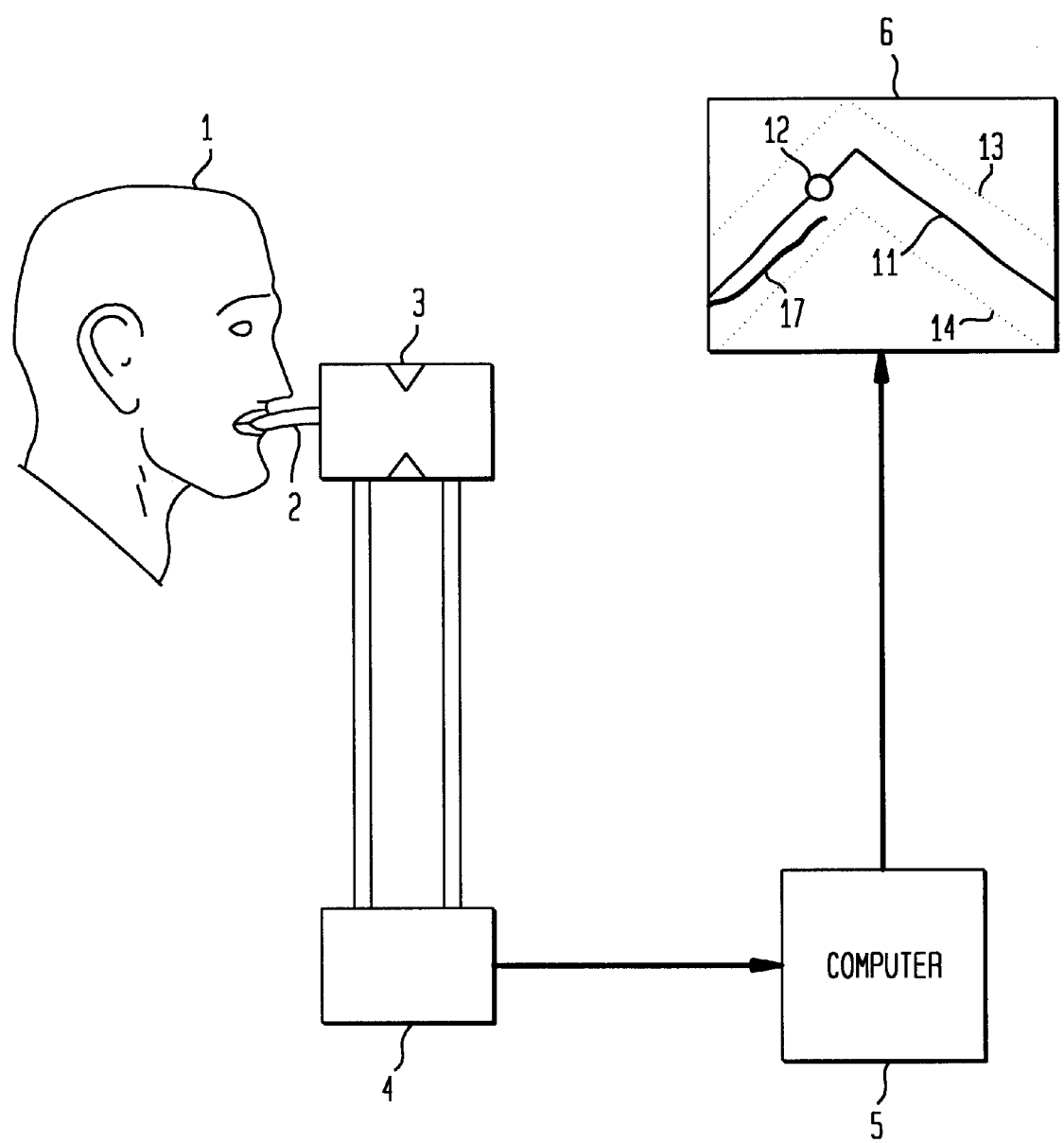

MINUTE VENTILATION

VENTILATOR BIOFEEDBACK FOR WEANING AND ASSISTANCE

This application claims benefit of provisional application 60/049,573, filed Jun. 13, 1997.

BACKGROUND OF THE INVENTION

This invention relates to improved methods and apparatus to monitor patients who are being weaned from ventilator support, or who are being treated with non-invasive ventilatory support in order to obviate the need for invasive intubation and controlled ventilation.

Hillsman incorporates by reference his U.S. Pat. No. 3,991,304 "Respiratory Biofeedback and Performance Evaluation System" and U.S. Pat. No. 4,984,158 "Metered Dose Inhaler Biofeedback Training and Evaluation System" and U.S. Pat. No. 5,582,182 "Abnormal Dyspnea Perception Detection System and Method." It has been discovered that full scale calibration of the breathing volume on the display ordinate axis and full scale display of the breathing rate on the abscissa axis is a particularly powerful standardized means to present breathing patterns for patient learning (See: "A Visual Biofeedback Method to Define and Teach Breathing Patterns;" Hillsman, Deane; Biological Psychology, v.43, Issue 3, Jun. 28, 1996, p.261) and "Clinical Experience With a Visual Biofeedback Method in COPD Rehabilitation;" Hillsman, Deane; Biological Psychology, v.43, Issue 3, Jun. 28, 1996, p.243–244).

Prior art with simple Tidal Volume visual biofeedback means has demonstrated effectiveness in weaning patients from ventilator dependancy (See: "The Reduction of Weaning Time from Mechanical Ventilation Using Tidal Volume and Relaxation Biofeedback;" Holliday, Jerome E. and Hyers, Thomas M.; American Review of Respiratory Diseases, 1990; v.141: p.1214–1220). The instant invention enhances this concept by sophisticated breathing pattern training.

Prior art traditional weaning techniques indicates the probability that some patients in the so-called "difficult to wean" category suffer from one or another form of poorly understood respiratory center dysfunction produced by severe illness such as shock, sepsis, etc. It is also apparent that the mode of ventilation used on these patients can have a significant influence, and in some manner may produce an undesirable breathing pattern imprint within the respiratory center which carries over into the weaning period.

In addition, many patients who fail to wean are known to have excessive neurologic drive from the respiratory center as measured by increased inspiratory effort by the so called P 0.1 test (the inspiratoxy pressure generated after a 0.1 second breath interruption) and increased electromyogram (EMG) activity of respiratory muscles. It seems this is probably in part related to corrupted neurologic driving signals from the respiratory center sending out strong but poorly coordinated and/or otherwise improper breathing pattern signals. An expression of this dysfunction is inefficient immediate rapid and shallow breathing displayed by many patients who fail to wean after being removed from ventilatory support, even though their respiratory muscular strength and pulmonary mechanics can be demonstrated to be adequate, and also by some erratic breathing patterns during this process. The instant invention provides proper breathing patterns to these patients as a model they will be able to follow, and therefore maintain adequate ventilation and permit effective participation the weaning process. And during this time the respiratory center will also be undergoing a training or reconditioning process to become more functional, thus further expediting complete removal from ventilatory support.

Ventilator dependence is a serious medical and economic problem. It is well known that severe and sometimes lethal complications may develop the longer a patient is on ventilator support. In addition, as ventilator therapy is provided in specialized and very expensive Intensive Care Unit environments, there is a strong economic need to minimize ventilator dependency. The instant invention therefore improves patient safety and minimizes expenses by more efficiently weaning patients from ventilator dependence.

While the instant invention is designed to work mainly with patients undergoing spontaneous breathing trials, it may also be used in patients undergoing weaning trials with partial assist from various ventilator devices. For example the so-called Proportional Assist Ventilator, or a ventilator with optional so-called Intermittent Mandatory Ventilation (IMV) or so-called Pressure Support Ventilation or similar modes, or an external non-invasive (i.e. no endotracheal tube or tracheostomy) ventilator such as the commercial BiPap device or a standard pressure controlled Intermittent Positive Pressure Breathing (IPPB) device used with a face mask, or a cuirass type ventilator. All of these prior art ventilators sense and/or adjust for respiratory deficiency in various ways, and provide appropriate inspiration assist breaths. But none of these ventilators provide direct patient incentives to breathe in a natural manner, and therefore are less efficient in the weaning process. The instant invention provides appropriate breathing prompting signals, and, when the patient fails in the weaning process the various independent safety and supportive functions of these ventilators become operative. In addition the instant invention could be used to more efficiently trigger the ventilatory supportive features of a plurality of prior art ventilators.

Prior art ventilator weaning monitoring methods are dearly inadequate, depending on subjective impressions of clinical fatigue or distress and/or arterial blood gas derangements that of necessity measure failure after the failure has already developed. More modem monitoring techniques such as the ratio of Tidal Volume to Respiratory Rate are still relatively crude indices of weaning performance. Weaning from ventilator dependency is potentially hazardous due to unexpected precipitous ventilatory failure, and early warning by appropriate monitoring means is imperative for patient safety. Further, controlled stress of weakened respiratory muscles is imperative in order to recondition these muscles, but in addition to not over-stress these fragile recovering muscles and therefore cause further damage. It is often difficult to safely define the proper degree of weaning stress clinically. The instant invention permits ideal levels of ventilation to be defined, as well as minimum safe levels of ventilation, and to provide visual monitoring and appropriate alarm signals of hazardous suboptimal ventilation on a breath by breath basis, prior to catastrophic and hazardous overall ventilatory failure. Patient performance is monitored using the so-called "Phantom Line" concept of performance quality control by use of visual plus and minus volumetric error limits. If instructions and encouragement from the caregivers fails to promptly correct the patient to a minimum safe level of ventilation, a physiologically appropriate level of fatigue is defined, and the weaning trial may be terminated prior to the development of excessive respiratory muscle fatigue. This will avoid the problem of excessive exhaustion with catastrophic and dangerous respiratory failure.

In the alternative, it may sometimes be desirable to extend the weaning period to maximally stress the patient's respiratory muscles. Prior art stressing techniques are highly subjective and not well defined, and are therefore in danger of producing excessive and damaging stress to the recovering respiratory muscles. The instant invention can define a maximum stressing goal by instantly substituting a visually similar breathing pattern with a smaller Tidal Volume breath and higher Respiratory Rate, which is the normal breathing pattern defense mechanism for fatiguing respiratory muscles. In this case a new level of optimal and minimal safe ventilatory level is defined and monitored to insure patient safety. When the patient demonstrates breath by breath ventilatory failure while using the natural defensive breathing pattern, a dear level of maximal stress has been defined and the weaning trial terminated.

Traditional prior art methods in acutely decompensated patients to avoid the need for invasive ventilatory support (i.e. with endotracheal intubation or tracheostomy) are clearly suboptimal. Typically a patient with emphysema and an acute bronchitic exacerbation is hospitalized with respiratory distress and a potential for need of life saving ventilatory support. However, it is well known if that patient can be managed for the first critical 24 hours by conservative means while various therapeutic modalities be given time to work, invasive ventilation can frequently be avoided, thereby avoiding well known ventilator complications and attendant increased cost. Typically these patients are struggling to breathe, and in so doing are resisting external ventilatory support means (e.g. the commercial BiPap device or a standard Intermittent Positive Pressure Breathing (IPPB) device) by poorly coordinated breathing that is out of phase with ventilator action, and therefore impairing the proper functionality of the vital external ventilation support. The same biofeedback system of the instant invention could be used equally as well in breathing control of these patients in acute respiratory failure, to coordinate patient and ventilator synchrony and thereby optimize ventilator action. Monitoring of such patients is likewise critically important and is similar to the monitoring as described with weaning protocols, but in this case the ventilatory failure parameters as described would result in a definable and logical decision for the need to intubate.

SUMMARY OF THE INVENTION

It is therefore one object of the present invention to provide sophisticated visual analogs of inspiration and expiration breathing patterns mimicking normal respiratory center function for subject visual biofeedback use in retraining a functionally impaired respiratory system and respiratory center, in order to enhance the weaning process from ventilator dependency.

It is another object of the invention to utilize this breathing control training in spontaneously breathing subjects being weaned from ventilator dependency.

It is yet another object of the invention to control ventilation in subjects being weaned with ventilatory assist devices using a variety of differing internal and external devices, and in so doing provide signals to the ventilatory assistive device as to the need for supportive ventilation when the patient's spontaneous ventilation is inadequate.

It is still another object of the invention to permit the graphic definition of an optimal level of ventilation as well as a minimal level of safe ventilation, and to sense and signal deficient ventilation on a breath by breath basis in order to monitor patient safety during the weaning process, and therefore to permit logical termination of the weaning trial if patient exhaustion or other factors prohibits adequate safe ventilatory levels.

It is further object of the invention to optionally stress the weaning process and enhance respiratory muscle strength retraining by instantly displaying a secondary modified breathing pattern with a reduced breathing volume level and increased respiratory rate, in order to mimic natural defensive breathing seen in respiratory muscle fatigue, while at the same time establishing new levels of optimal ventilation and minimal safe ventilation.

It is additional object of the invention to have the secondary modified breathing pattern appear similar to the initial breathing pattern due to a unique method of displaying the "primary breathing pattern" (respiratory tidal volume and rate) as full scale abscissa and ordinate visual displays, while maintaining the original "secondary breathing pattern" (respiratory inspiration to expiration time ratio, end inspiratory and end expiratory breath hold time, and inspiratory and expiratory waveforms), thus permitting the patient to continue practicing with a constant visual analog breathing pattern throughout the entire weaning trial.

It is further additional object of the invention to permit controlled spontaneous weaning trials in patients being weaned by ventilator assistive means, as a definitive test of spontaneous ventilation, prior to extubation and removal from mechanical ventilation.

It is yet a further object of the invention to be used with stand-alone respiratory flow sensing transducers in the patient's airway, or optionally with transducers that are a part of the ventilator system, or with external motion sensing transducers on the chest wall, all of which have been calibrated to represent correct breathing volumes.

It is a final object of the invention to visually biofeedback prompt and monitor patients in acute respiratory failure who are being treated with external non-invasive respiratory assistive devices, to coordinate patient and ventilator action and thus permit optimal ventilator action, in an attempt at conservative management and avoidance of invasive endotracheal intubation and controlled ventilation.

These objectives are achieved by a computer based controlling system that displays the desired breathing patterns, with cursor prompting of desired performance, and simultaneous real time patient performance for patient visual biofeedback breathing control and training. The breathing pattern display could be a standard volume versus respiratory rate display wherein the breath volume and rate are proportionately displayed. However, in the preferred embodiment the breath volume and respiratory rate are both displayed full scale to create a standardized breathing pattern display, as this type of display has been discovered to enhance breathing pattern training and imprinting of the desired physiologic parameters.

Multiple different breathing patterns may be preprogrammed and instantaneously displayed. Adjustable plus and minus error limit visual analogs above and below the optimal visual analog pattern (expressed as a percentage of the Tidal Volume breath) permit definition of the lowest level of safe ventilation for monitoring purposes. On a breath by breath basis it is visually apparent, and with optional monitoring alarms, if the patient is not achieving minimum safe Tidal Volume ventilatory goals, or alternatively by real time minute to minute display of the actual Minute Ventilation as calculated from summed actual Tidal Volumes. In this manner corrective action may be promptly taken before the onset of overall hazardous ventilatory failure, by either ventilatory assistive devices or patient encouragement of spontaneous breathing efforts from the caregivers. If continued failure to achieve minimum respiratory goals is not achieved then a definable and logical end point of the weaning trial can be made before the patient is in danger due to acute ventilatory failure.

Optionally in a patient failing to achieve minimum ventilatory goals, the breathing pattern may be switched to one with a smaller Tidal Volume and increased Respiratory Rate, in order to mimic the natural defense mechanism of fatiguing respiratory muscles, thus permitting additional stress of the respiratory muscles in order to further train them for eventual complete weaning from the ventilator. However, during this additional trial the breathing pattern appears identical to the original pattern, thus permitting the patient to train with a constant visual breathing analog.

The ability of the device to provide a constant visual pattern despite the changing Tidal Volume and Respiratory Rate is due to a unique display wherein the so-called "Primary Breathing Pattern" composed of the Tidal Volume and Respiratory Rate are always displayed full scale on the "y" ordinate and "x" abscissa axis respectively. The breathing pattern will appear identical despite volume and rate changes if the so-called "Secondary Breathing Pattern" components of inspiration to expiration time ratio, end inspiration and end expiration breath hold times, and inspiration and expiration waveform analogs are set in an identical manner to the original breathing pattern. It has been discovered this method of breathing pattern display is particularly efficient in patient training and imprinting of breathing patterns.

These and other objects of the invention will be seen in the following description and in the drawing.

THE DRAWING

FIG. 1 is a simple schematic diagram of the overall stand-alone system measuring spontaneous breathing;

Figure 3A:
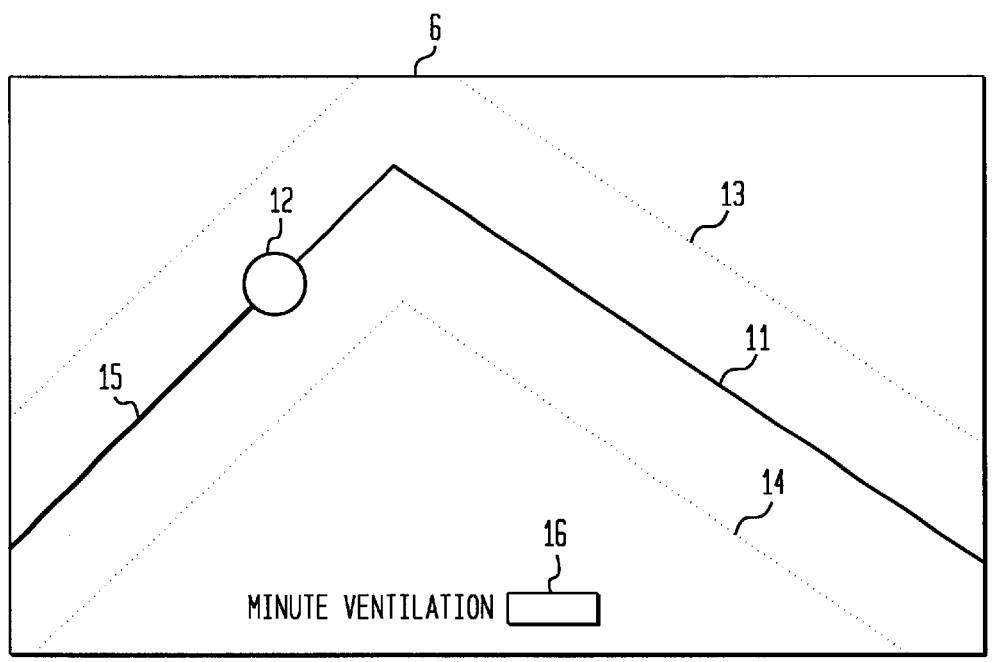
Figure 3B:
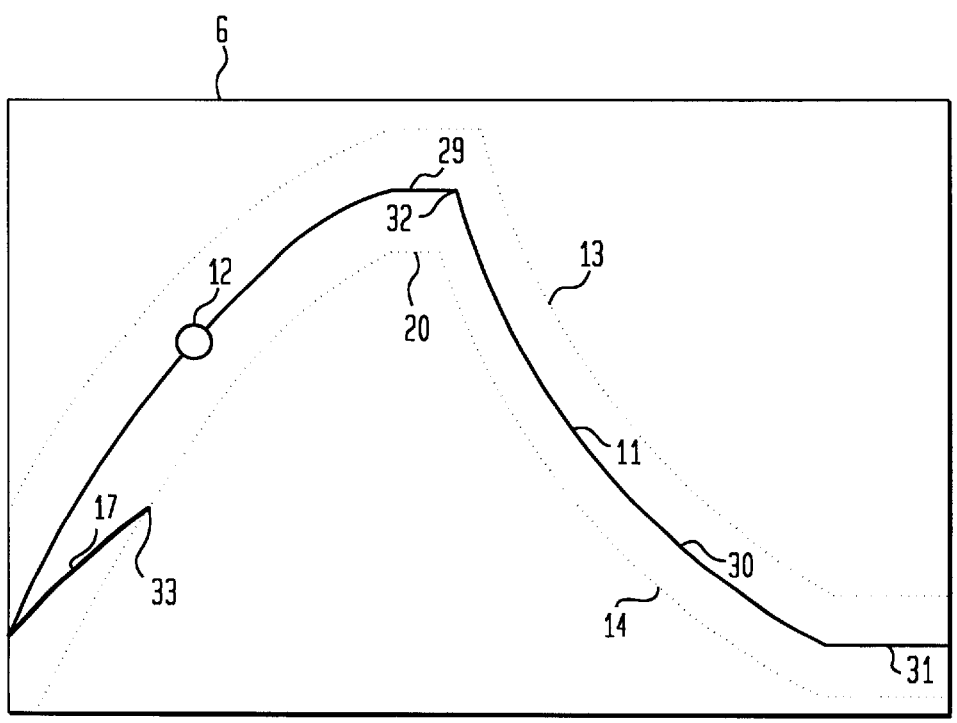
Figure 4A:
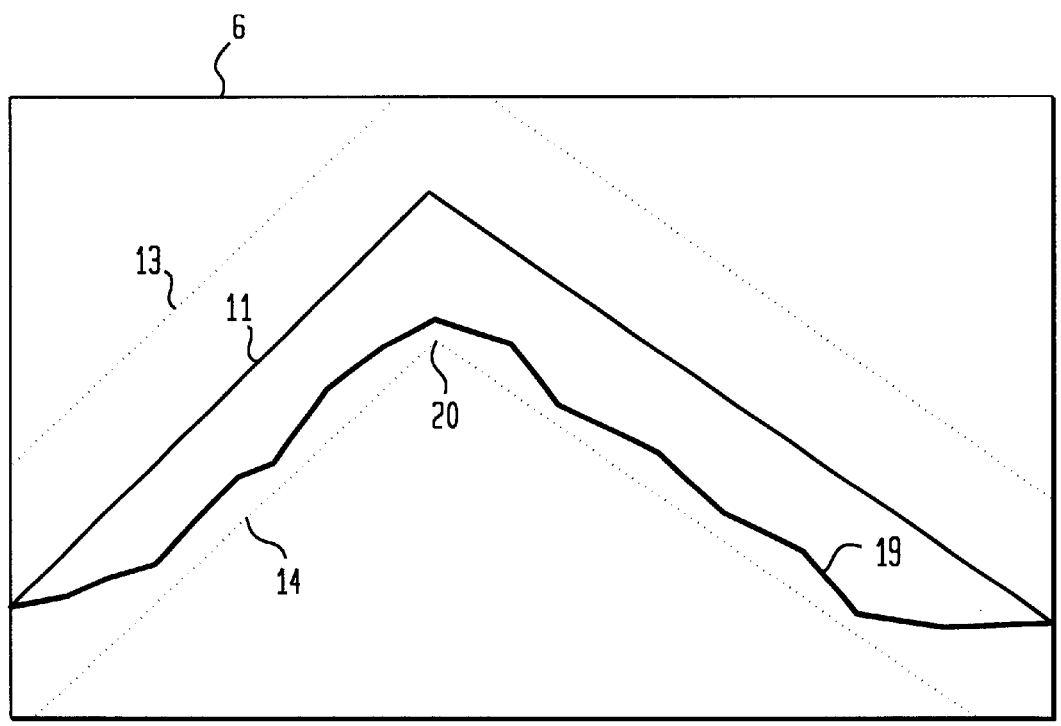
Figure 4B:
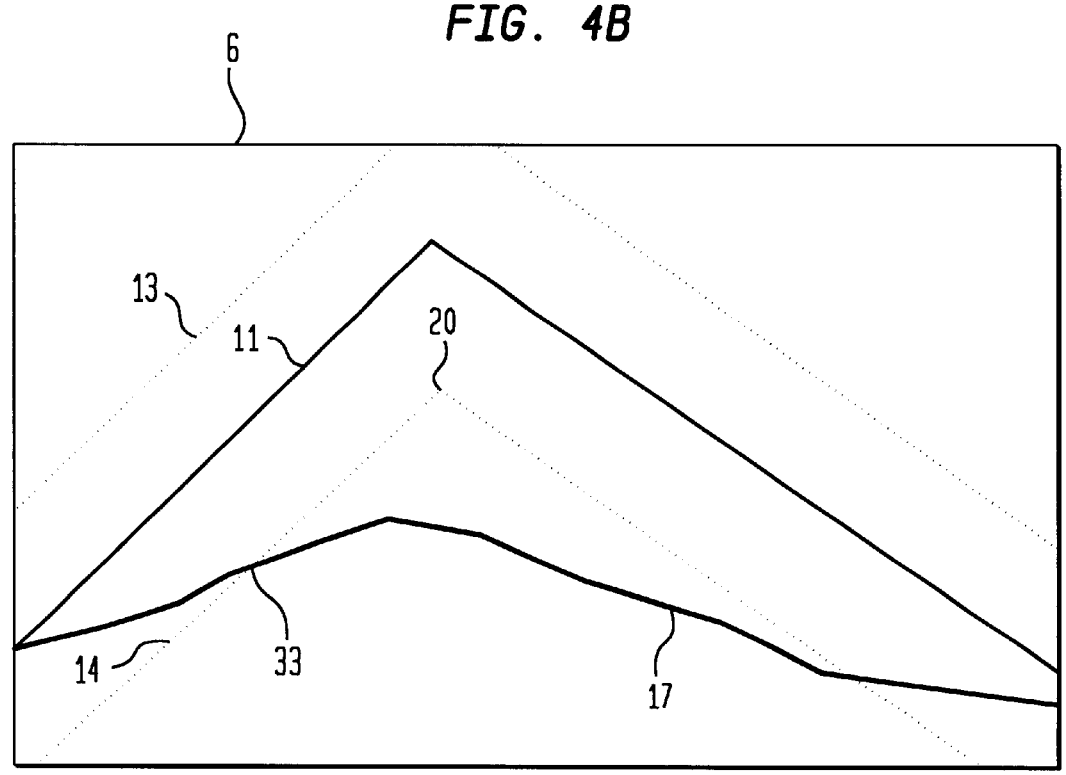
Figure 5A:
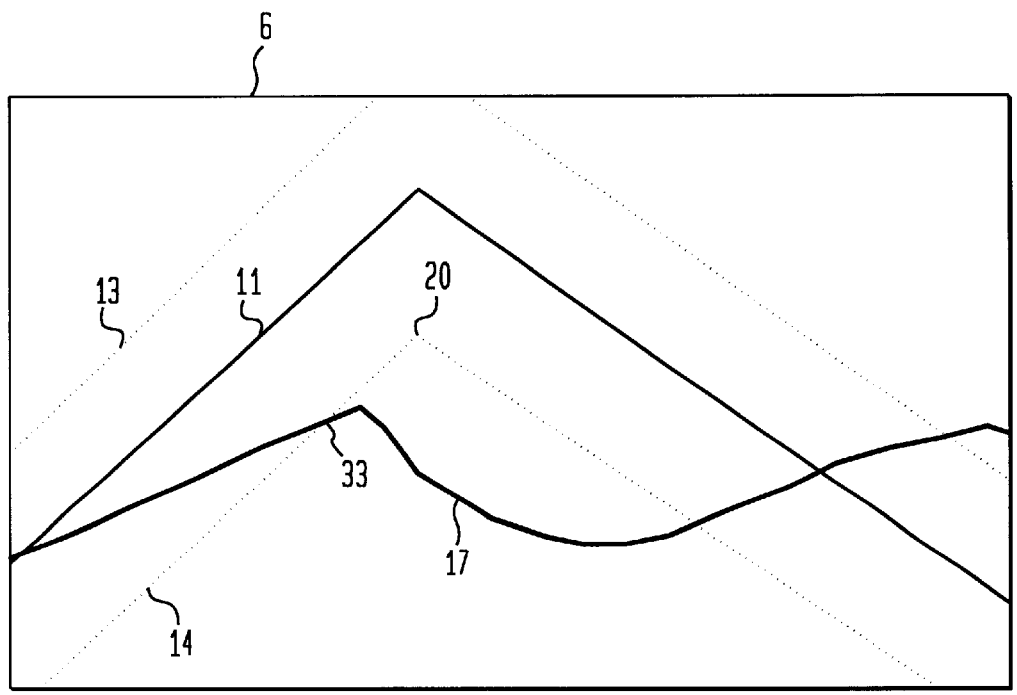
Figure 5B:
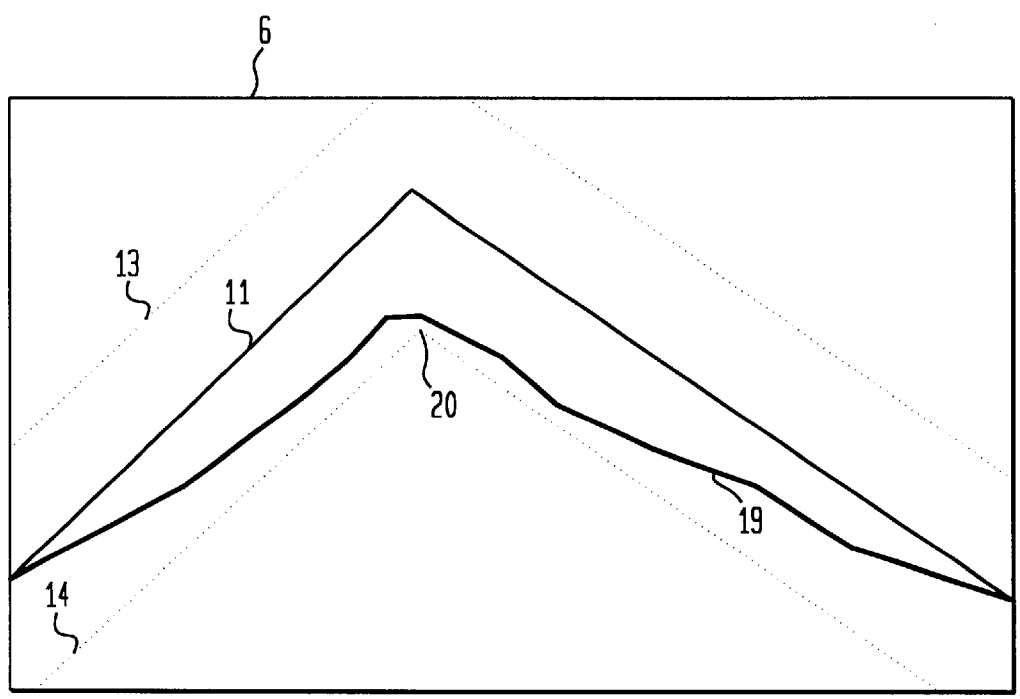
Figure 6:
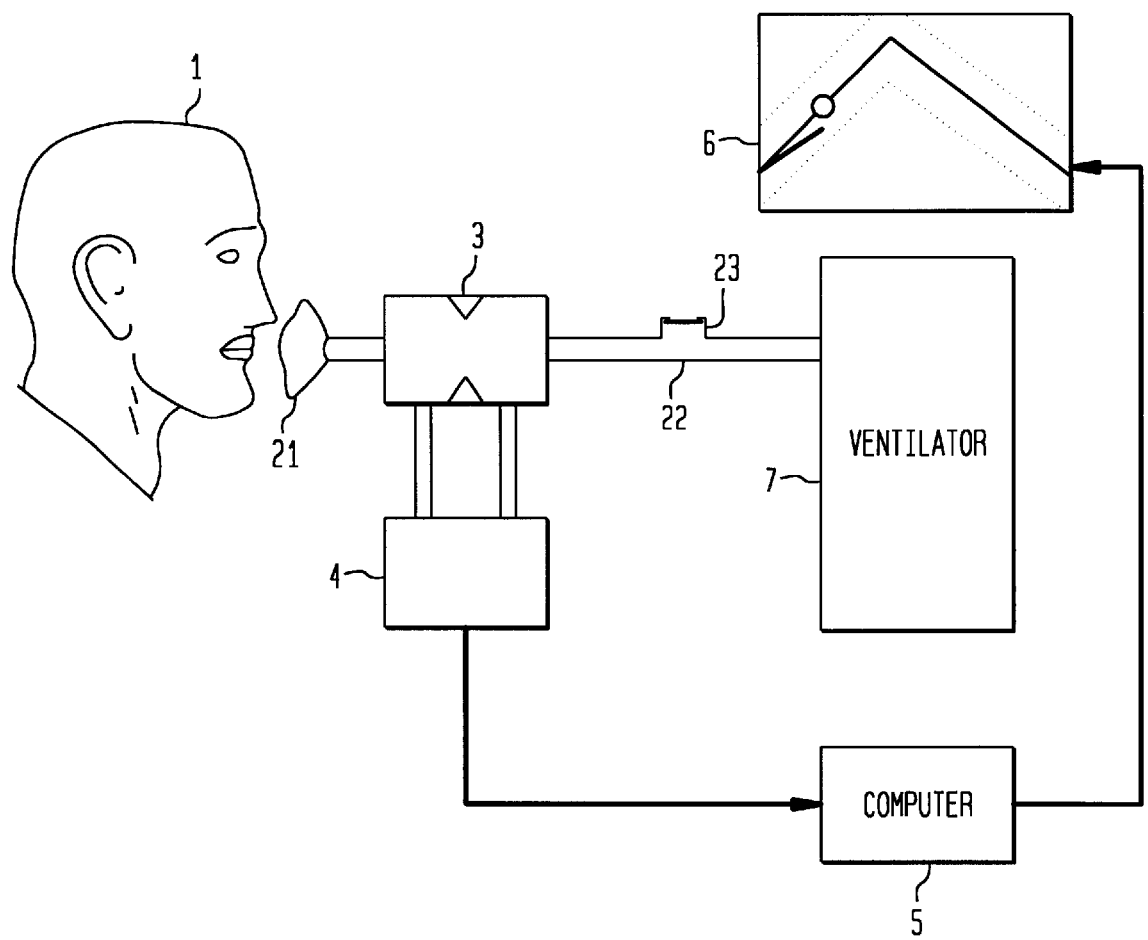

FIG. 3a is a view of the computer display showing a simple linear breathing program, with plus and minus visual Phantom Line error detection limits, a prompting cursor with good patient performance, and a Minute Ventilation display of actual ventilation, and FIG. 3b is a similar view of the computer display showing a complex breathing program representative of an actual breathing pattern, and demonstrating suboptimal breathing performance being detected by the lower error limit Phantom Line;

FIG. 4a is a view of the computer display showing a simple linear breathing program, demonstrating suboptimal patient breathing performance, but not activating the lower error limit Phantom Line, and FIG. 4b is a view of the computer display showing a simple linear breathing program, demonstrating suboptimal patient breathing performance, now activating the lower error limit Phantom Line;

FIG. 5a is a view of the computer display showing a simple linear breathing program, demonstrating suboptimal patient breathing performance, activating the lower error limit Phantom Line, and FIG. 5b is a view of the computer display showing an identical appearing simple linear breathing program, even though the Tidal Volume is now smaller and Respiratory Rate increased, demonstrating the same level of patient breathing performance no longer activating the lower error limit Phantom Line;

FIG. 6 is a simple schematic diagram of the overall system using a ventilator connected to the patient with an external face mask, and utilizing flow transducers in line with the face mask and ventilator.

DESCRIPTION OF PREFERRED EMBODIMENTS

In the following description, metric units and standard respiratory nomenclature as defined by the American College of Chest Physicians are employed unless otherwise stated. Particular attention is directed toward the evaluation of human subjects undergoing so-called "weaning" from mechanical ventilator dependence, and human subjects with acute respiratory failure using non-invasive ventilatory assist devices.

Many patients requiring life saving ventilator therapy experience difficulty in the weaning process from ventilator dependence. This is a serious medical problem, as it is well established the longer a patient remains ventilator dependent the higher the rate of complications and fatality. In addition there are significant financial implications as ventilator therapy is typically performed in high cost Intensive Care Units.

The reasons for ventilator dependence are complex, and range from lung damage to general problems of debilitating systemic illness such as shock, sepsis, renal failure, malnutrition and the like. In addition respiratory muscle weakness and dysfunction play a prominent role. However, a significant number of patients who appear to have adequately restored general and pulmonary health, and adequate respiratory muscle function, fail in the weaning process. Particularly puzzling is evidence that in many of these patients there appears to be excessively strong neurologic driving signals to the respiratory muscles from the controlling respiratory center. It is apparent the respiratory center itself in these patients may be dysfunctional. Apparently, even though the respiratory center may be sending excessively strong signals, in a manner that is poorly understood, these signals are corrupted in terms of abnormal breathing patterns and coordination. It follows that any method to restore normal respiratory muscular activity and respiratory center functionality would be important in the weaning process.

The weaning process itself uses either spontaneous breathing trials of so-called T-Piece Weaning, or with weaning ventilatory support using one or another ventilators or ventilatory assistive devices. The ventilators might be of various types, for example the so-called Proportional Assist Ventilator, or any ventilator that has the capability of the so-called Pressure Support Ventilation mode or so-called Intermittent Mandatory Ventilation (IMV) mode or similar ventilatory modes, or in fact any ventilator that provides positive pressure assist such as the standard pressure controlled Intermittent Positive Pressure Breathing (IPPB) device or the commercial BiPap device. The ventilatory support could also be provided by an external cuirass type ventilator.

An underlying concept of the instant invention is to provide sophisticated prompting analog visual signals of breathing patterns closely mimicking normal breathing patterns and breathing timing, and to use these breathing patterns in a visual biofeedback manner to restore and re-train normal respiratory muscular function and respiratory center function during the process of weaning.

In the preferred embodiment the patient is provided with sophisticated analog breathing patterns mimicking normal breathing patterns which are then used by the patient in a visual biofeedback manner as generally described in Hillsman's U.S. Pat. No. 3,991,304. This could be in a standard volume/time display wherein the volume and time parameters are proportionately displayed, i.e. large breaths appear large and small breaths appear small and, rapid breathing is indicated by multiple waveforms and slow breathing indicated by fewer waveforms. It has been discovered that displaying the breath volume and respiratory rate full scale on the ordinate and abscissa axis respectively creates a unique standardized breathing display with novel properties of facilitating patient biofeedback learning of breathing patterns. In an alternate embodiment the breathing pattern display could also be shown in a standard manner, that is, without the internal calibration to full scale display of breath volume and respiratory rate full scale on the ordinate and abscissa axis.

Briefly, a desired breathing pattern may be synthesized by inputting Tidal Volume and Respiratory Rate to generate a so-called "Primary Breathing Pattern" as indeed all breathing patterns are of necessity composed of these two primary parameters. Tidal Volume is displayed full scale on the "y" axis ordinate, and Respiratory Rate cycle time full scale on the "x" abscissa axis. The result therefore is that all Primary Breathing Patterns appear the same, whether they be large/slow breaths or small/rapid breaths, thereby providing a universally standard display for the most fundamental aspects of breathing patterns. The precise individual visual analog of breathing may then be generated by inputting the Inspiration to Expiration Time Ratio, end Inspiration and end Expiration Breath Hold time durations, and Inspiration and Expiration individual linear or various curvilinear waveforms, to create a unique so-called "Secondary Breathing Pattern." This programmed breathing pattern is displayed, along with a prompting cursor moving in real time along the visual analog prescription, and simultaneously the patient's real time breathing performance is displayed. The patient attempts to match their performance with the programmed analog in a visual biofeedback training manner, and in so doing learn and imprint the desired breathing pattern. A multitude of different breathing patterns may be stored and instantly displayed. Quality control of patient performance may be evaluated by optionally placing plus and minus visual error limits (expressed as a percentage of the Tidal Volume) above and below the desired program analog, and optionally sounding an alarm if the defined error limits are exceeded.

The preferred embodiment would be a stand-alone device with it's own flow sensing transducer attached to the endotracheal tube or tracheostomy of the patient undergoing a spontaneous weaning trial, or alternatively from external sensors detecting movement of the chest wall.

In another preferred embodiment the stand-alone device would work in conjunction with a ventilator device, or ventilatory assistive device. Optionally the breathing sensing transducers of the ventilatory device could be the input to the biofeedback device. In addition, the breathing transducer signals from external chest motion sensing devices, for example the commercial Respitrace device, could be input to the biofeedback device, without departing from the inventive concept. Here the invention acts as an adjunct to the normal operation characteristics of a multitude of ventilators with differing ventilatory modes and alarm systems, by providing the visual biofeedback signals to encourage desired breathing performance, and the adjunct breath by breath monitoring capabilities as described. If the patient is undergoing continuous so-called Pressure Support or similar continuous modes of ventilatory support the invention would act only to synchronize and optimize patient and ventilator interaction. However, if the patient failed in the weaning trial then the normal functions of ventilator backup support would activate independently.

The best mode of weaning remains controversial. Some physicians prefer spontaneous breathing weaning trials, while other physicians prefer one or another modes of assistive ventilation during weaning. This invention is designed to accommodate both schools of thought, while adding the feature of biofeedback corrective breathing patterns to both.

Ventilator weaning is an inherently dangerous process, as weakened respiratory muscles may abruptly fail and the patient therefore suffer acute respiratory failure. At the same time the respiratory muscles must be stressed in order to be strengthened, and it is frequently clinically difficult to judge how much controlled stress can be applied before terminating the weaning trial. It is imperative therefore to be able to establish a lower limit of safe ventilation, and to be able to follow the patient's attempts to ventilate on a breath by breath basis to see if the minimum safe level of ventilation is achieved. This is done by setting the Phantom Line error detection option to a lower limit of Tidal Volume acceptable safety, and visually determining on a breath by breath basis if the patient is succeeding in his effort to breathe a minimum level of acceptable Tidal Volume. In this manner advanced warning of weaning failure will be possible as the patient develops progressive fatigue and respiratory failure, prior to the onset of exhaustion and overall ventilatory failure. Optionally there may be an alarm sounded if the patient is not succeeding. In addition it is desirable to know the actual level of achieved Minute Ventilation (i.e. Tidal Volume×Respiratory Rate) on a minute by minute basis, by summing the actual Tidal Volumes over the past minute. Optionally this value can be stored and displayed to follow trend analysis during the weaning trial. In this manner a decision to terminate the weaning trial can be made easily and objectively, before the onset of outright ventilatory failure, thus minimizing patient vulnerability to undetected hazardous ventilatory failure.

Should a patient be failing in the weaning trial by not achieving minimum safe levels of ventilation, it may still be judged desirable to extend the weaning trial in order to further stress and recondition the respiratory muscles. On the other hand, it is important to not over stress the recovering respiratory muscles and further impair their recovery. In this case the breathing pattern could be switched to one with a lower Tidal Volume and higher Respiratory Rate, to essentially mimic the natural defense mechanism employed by fatiguing respiratory muscles. Here only the Primary Breathing Pattern is altered. If the Secondary Breathing Pattern parameters are identical to the original, the patient will therefore perceive this new breathing pattern as identical. This apparent identical visual analog is highly desirable in order to continue to imprint a particular breathing pattern in an uninterrupted manner, and therefore facilitate the respiratory center training process. Of necessity, the new lower limits of safe Tidal Volume requirements on the Phantom Line display will now be in a hazardous range, and any failure to meet these minimum Tidal Volume respiratory goals is a dear indication to immediately terminate the weaning process.

The other underlying concept of the instant invention is ventilatory pattern biofeedback prompting for patients in acute respiratory failure who have inefficient breathing patterns that prohibit the proper use of ventilatory assist devices. This same system could be used equally as well in breathing control of these patients, where attempts are being made to assist such patients with non-invasive ventilatory support, in order to avoid invasive endotracheal intubation and controlled ventilation.

Typically these acute respiratory failure patients have severe Chronic Obstructive Pulmonary Disease (COPD) such as Emphysema who have developed a bronchitic infection exacerbation that causes them to decompensate. Typically they are admitted to hospital in respiratory distress, exhausted, and choking on retained excessive bronchial mucus. An urgent decision must frequently be made as to whether or not these patients require immediate intubation and ventilation as a life saving measure. However, committing a patient to a course of invasive intubation and controlled ventilation has certain well known risks, and certainly is very expensive therapy as it takes place in the Intensive Care Unit environment. Avoiding intubation and treating these patients conservatively is therefore highly desirable, but the decision of whether or not to intubate can be a very subjective and difficult one. It is well known that many such patients will significantly improve with intensive therapy in the first day of admission, after clearing bronchial mucus and permitting time for a multitude of drugs to take effect. The clinical problem therefore is the need for effective non-invasive (i.e. no endotracheal intubation) ventilatory support to a patient who is acutely ill and usually exhausted, and who may suffer catastrophic and life threatening final respiratory decompensation at any moment.

Monitoring of such patients therefore is critically important and is similar to the monitoring process as described with weaning protocols, but in this case the ventilatory failure parameters as defined would result in a definable and logical decision for the need to intubate. In addition, should the patient fall asleep, the breathing pattern can be immediately switched to one that defines a minimal level of safe ventilation, and the patient monitored accordingly. And in conjunction with the usual serial arterial blood gas measurements in such cases, the physician will derive much better insight as to how ventilatory performance equates to the patients ability to eliminate carbon dioxide and oxygenate their blood.

As to non-invasive ventilatory support, for example with the commercial BiPap device or a standard pressure controlled and limited Intermittent Positive Pressure Breathing (IPPB) device, this is administered by a face mask or nasal mask These and similar ventilators may be set to deliver a given breath volume at a set respiratory rate, or to trigger inspiration on detecting negative mouth pressure at the beginning of inspiration. Typically the patient is struggling to breathe with rapid, shallow and frequently irregular breaths. This manner of breathing does not permit effective ventilator action. For example, if the patient is breathing out as the ventilator is trying to deliver an inspiratory breath, the patient and ventilator are working at cross purposes and therefore the volume of air delivered from the ventilator will be suboptimal. This is particularly so if the ventilator has a sensing mechanism to shut off the inspiratory flow if premature excess inspiratory delivery pressure is detected. Effective ventilator therapy therefore requires the patient to coordinate their breathing with ventilator activity, and to perform their breathing efforts in a manner that will not cause premature or excessive inspiratory pressure. This is is achieved by providing proper breathing patterns (generally larger Tidal Volumes at a slower respiratory Rate, and a prolonged expiratory phase to permit full lung exhalation to avoid so-called "air trapping" with subsequent inefficient dynamic overinflation of the lungs) to the patient, by using patient biofeedback control and monitoring to be certain that indeed optimal ventilator therapy is being safely achieved. In addition, a multiple of breathing patterns may be preprogrammed and displayed for specific purposes. For example, one breathing pattern may be optimized for patient interaction with the assistive breathing device in an aerosol delivery therapeutic application, and another for when the patient is resting, and yet another when the patient is sleeping and the like.

Referring to the simplified schematic diagram in FIG. 1 which is an individual stand-alone device, the Patient (1) breathes spontaneously through Endotracheal Tube (2) which is connected to a Flow Transducer (3), the differential pressure from which is transmitted to Differential Pressure Transducer (4) which in turn inputs electronic flow data to Computer (5) which in turn integrates the flow information into volumetric Tidal Volume data. The real time breathing Tidal Volume is displayed on computer CRT Visual Display (6) plotted against the actual time of each individual breath. Also shown is the desired Inspiration/Expiration Program Analog (11) which is internally calibrated to a full scale ordinate Tidal Volume display and likewise full scale abscissa Respiratory Rate display, refreshing the display at the appropriate programmed breath to breath interval. Also shown is Cursor Prompt (12) and Positive Phantom Line Error Limit (13) and Negative Phantom Line Error Limit (14). The Patient (1) observes CRT Visual Display (6) and thereby is able to receive visual biofeedback prompting from the real time Suboptimal/Deficient Patient Performance display (17) as described below. The monitoring personnel may likewise observe the display to see if patient performance is satisfactory and to determine if the subject is meeting minimum performance requirements as defined by the Phantom Lines. This configuration is designed for subjects breathing spontaneously, and therefore only respiratory monitoring and visual biofeedback prompting is possible, this in conjunction with attending staff who may then use human intervention and the monitor display to encourage the patient to better performance. Essentially the attending staff may accurately visualize the real time details of the patients respiratory performance on a breath by breath basis, which is much superior to the traditional methods of weaning monitoring such as noting facial expressions for anxiety or distress, chest movement, chest auscultation of breath sounds, or intermittent measurement of simple respiratory parameters such as Tidal Volume or Respiratory Rate.

Figure 2A:
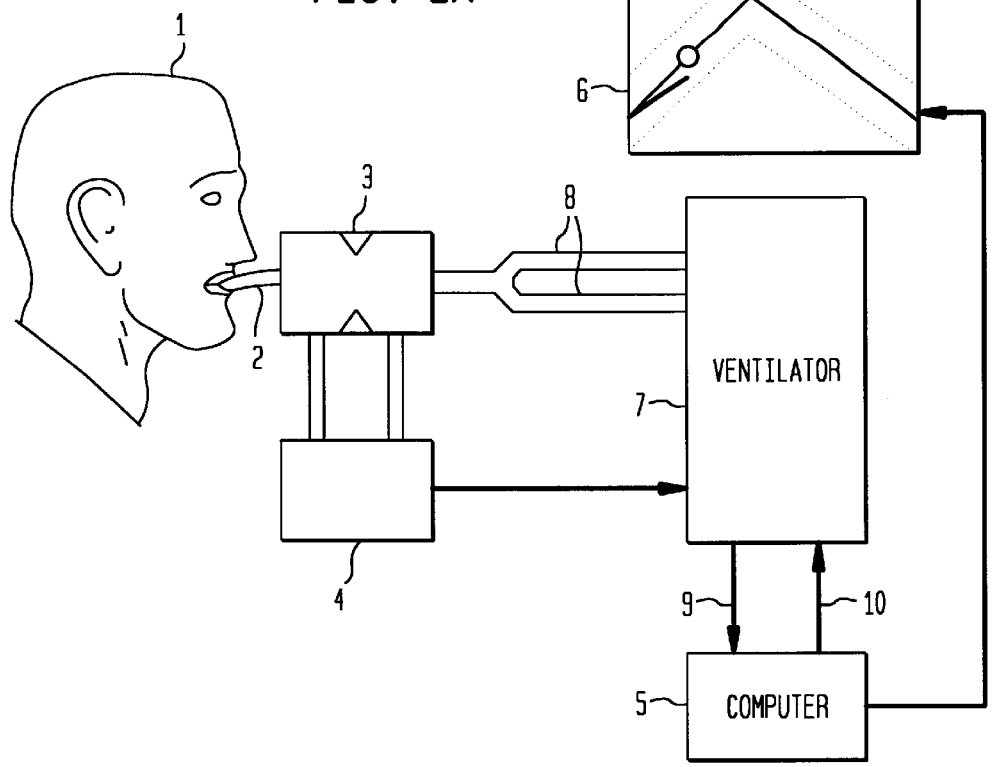
FIG. 2a is a simple schematic diagram of the overall system using a ventilator, and utilizing flow transducers from the ventilator device.

Referring to the simplified schematic diagram in FIG. 2a which is the same basic individual stand-alone visual biofeedback system, but now additionally working in conjunction with a ventilator assistive device. Patient (1) is connected by Endotracheal Tube (2) through Flow Transducer (3) to Ventilator (7) by Inspiration/Expiration Ventilator Hoses (8). Spontaneous ventilation is permitted through standard Inspiration and Expiration ports in the ventilator (7) breathing circuitry (not shown), or if used in a continuous support ventilator such as Pressure Support ventilation via the usual circuitry of such ventilators (not shown). Differential Pressure Transducer (4) sends electronic flow signals to the Ventilator (7) or directly to Computer (5) (not shown) to derive Tidal Volume data. Computer (5) receives data from Ventilator (7) via Flow Data from Ventilator (9) and interacts back to Ventilator (7) via Feedback Logic (10) and likewise provides visual display data to CRT Visual Display (6).

In an alternate embodiment the Flow Transducer and Differential Pressure Transducer (not shown) are internal component parts of the ventilator monitoring system, which in turn provides respiratory Flow Data and/or integrated volumetric Flow Data from Ventilator (9) component parts to Computer (5) which may also be an integral part of the ventilator (not shown). In this embodiment, the invention becomes a software component part of the Ventilator computer control system. Computer (5) provides volume and time data for display on CRT Visual Display (6), but in addition provides Feedback Logic (10) to Ventilator (7) to activate and/or modify the ventilator performance to provide assistive breaths should the patient's spontaneous breathing performance fall below a minimal level of Tidal Volume and/or Minute Ventilation. For example, the system could be programmed to trigger assistive breathing if the patient failed to meet minimum safe Tidal Volumes for three successive breaths.

Figure 2B:
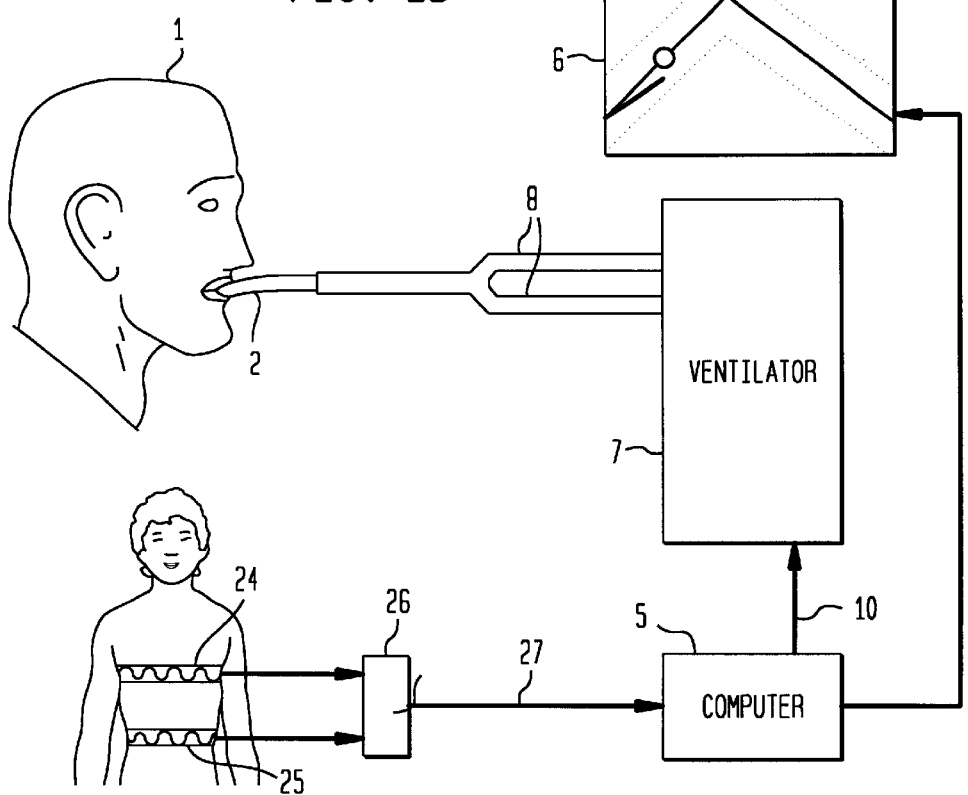
FIG. 2b is a simple schematic diagram of the overall system using a ventilator, and utilizing motion transducers from an external chest wall sensing device calibrated to measure Tidal Volume breaths.

Referring to the simplified schematic diagram in FIG. 2b the same basic system is used in conjunction with a Ventilator (7), but in this case the breathing sensing means is by external transducers on the chest wall. These external transducers could be of many types, all basically sensing motion. For example, devices that sense pressure changes within dosed tubes or chambers attached to the chest that are pressurized with movement and calibrated to reveal volume. Shown is another type of commercial device, the Respitrace system. A Chest Motion Transducer (24) and Abdomen Motion Transducer (25) send electronically activated signals from sensing wires that have been woven into chest and abdominal expandable fabric bands to a Signal Processor (26), which in turn combines the signals into a Summed Tidal Volume Signal (27) which is input to Computer (5) and thereafter is used in the overall patient display and ventilator system as described above under FIG. 2a.

Referring to the diagram in FIG. 3a which is a CRT Visual Display (6) showing a simple linear breathing pattern prescription as noted in the Inspiration/Expiration Program Analog (11). Tidal Volume is displayed on the "y" ordinate axis, and is always displayed full scale. Respiratory Rate, (or respiratory Duty Cycle) is the display refresh time and is also always displayed full scale on the "x" abscissa axis. These two essential parameters comprise the so-called "Primary Breathing Pattern," and is a unique way of displaying these fundamental respiratory parameters in a unifying manner that appears identical whether the breath is large and slow or small and rapid. A Cursor Prompt (12) moves along the Inspiration/Expiration Program Analog (11) in real time, and is depicted here on the inspiration portion of the waveform analog. Patient real time breathing performance is also displayed, and in this case Optimal Patient Performance (15) is shown by a matching of the patient performance analog on the breathing prescription analog (11). Also shown are dotted plus and minus Phantom Line error limits (13 and 14 respectively), which are percentage volumetric errors based on the maximal Tidal Volume defined. For example, for a 1,000 cc Tidal Volume a +/−25% error limit would be 250 cc throughout the entire respiratory cycle. The Positive Phantom Line Error Limit (13) and Negative Phantom Line Error Limit (14) is displayed, and in this case they would be 1,250 and 750 cc's with respect to the maximal Tidal Volume. These 250 cc error limits are displayed equidistant from the programmed Inspiration/Expiration Program Analog (11) throughout. Also shown is a numeric Minute Ventilation Display (16) which is the minute by minute actual Minute Ventilation, calculated by summing the previous minute of actual Tidal Volumes. This Minute Ventilation data may be stored, and optionally sequentially displayed for trend analysis.

Referring to the diagram in FIG. 3b which is a CRT Visual Display (6) showing a complex breathing prescription, which is representative of an actual physiologic breathing pattern, as noted in Inspiration/Expiration Program Analog (11). This breathing analog is composed of a curvilinear Inspiratory Waveform (28), an end Inspiration Breath Hold (29), a curvilinear Expiration Waveform (30), and an End Expiration Breath Hold (31), all within a particular Inspiration: Expiration Time Ratio (32). These adjustable parameters comprise the so-called "Secondary Breathing Pattern" which gives the overall breathing pattern it's unique visual analog complexity within the Primary Breathing Pattern. Note that changing the Inspiration: Expiration Time Ratio (32) position along the "x" abscissa axis will produce subtle alterations in all of the remaining Secondary Breathing Pattern parameters. Cursor Prompt (12) on the Inspiration Waveform (28) highlights Suboptimal/Deficient Patient Performance (17) crossing the Negative Phantom Line Error Limit (14) and being detected at Error Detection Point (33). Note this is below the Minimum Safe Tidal Volume (20) point requirement.

Referring to the diagram in FIG. 4a which is a CRT Visual Display (6) showing a simple breathing prescription Inspiration/Expiration Program Analog (11) with Suboptimal but Adequate Patient Performance (19) as the patient performance did not fall below the Negative Phantom line Error limit (14), and in particular did not fall below the Minimum Safe Tidal Volume (20) point.

Referring to the simplified diagram in FIG. 4b which is a CRT Visual Display (6) showing a simple breathing prescription Inspiration/Expiration Program Analog (11) with Suboptimal/Deficient Patient Performance (17), as this patient performance is below the Negative Phantom Line Error Limit (14) as first detected at Error Detection Point (33). In particular note that the Minimum Safe Tidal Volume (20) point has not been achieved, and this is easily and immediately visually apparent. In a ventilator assistive system this failure to achieve the required safe level of Tidal Volume could sound an appropriate alarm, and be optionally programmable to activate a ventilator safety backup system after a programmable series of consecutive deficient breathing performances (e.g. 3 to 5 deficient breaths), and therefore cause the ventilator to activate and supplement patient efforts to achieve safe ventilatory levels.

Referring to the diagram in FIG. 5a which is a CRT Visual Display (6) showing a simple breathing prescription Inspiration/Expiration Program Analog (11) with Suboptimal/Deficient Patient Performance (17), as this patient performance is below the Negative Phantom Line Error limit (14) as first detected at Error Detection Point (33). In particular note that the Minimum Safe Tidal Volume (20) point has not been achieved. This shallow and rapid breathing pattern is typical of a patient developing respiratory muscle exhaustion. In this case, assume the physician decided to attempt weaning with at Tidal Volume of 700 cc, and Rate 12, and therefore a Minute Ventilation of 8.4 LPM (700×12=8.4). By providing a +/−25% error limit, the Phantom Line lower peak Tidal Volume error limit, the Minimum Safe Tidal Volume (20) is 525 cc (i.e. 700×0.25=175; 700−175=525). This defined minimal ventilation will result in a Minute Ventilation of 6.3 LPM (525×12=6.3) which for an average adult patient in a weaning situation would probably be at a level of mild hypoventilation and $CO_2$ retention, which could easily be confirmed by parallel arterial blood gas measurements. If urging by the nursing or respiratory therapy staff failed to get the patient effort within the safe ventilation range, there would then be an objective measure of exhaustion and the weaning trial could then be safely terminated. Optionally on a breath by breath basis an alarm could be sounded for failure to stay within the defined minimum safe Tidal Volume safety parameters (i.e. below the Minimum Safe Tidal Volume (20) error limit), and as well the Minute Ventilation trend analysis using the sum of the last minute of actual Tidal Volumes could be displayed and trend displayed on a minute by minute basis as depicted in FIG. 3a Minute Ventilation Display (16).

Referring to the diagram in FIG. 5b which is a CRT Visual Display (6) showing a simple breathing prescription Inspiration/Expiration Program Analog (11) with the patient continuing to breathe in an identical manner as in FIG. 5a. The Inspiration/Expiration Program Analog, and Positive Phantom Line Error Limit (13) and Negative Phantom Line Error Limit (14) appears identical to the FIG. 5a display, even though the Primary Breathing Pattern parameters have been altered to a lower Tidal Volume and increased Respiratory Rate, due to the fact that the Secondary Breathing Pattern parameters have not been changed. For example, the new program might be a Tidal Volume of 400 cc, Rate 15, and with a resultant Minute Ventilation of 6.0 LPM. With a +/−25% error, the lower defined Tidal Volume limit is now 4.5 LPM (400×0.25=100; 400−100=300; 300×15=4.5). With these new parameters the patient's visually identical level of breathing now appears as a new Suboptimal but Adequate Patient Performance (19), and there is now a new lower Minimum Safe Tidal Volume (20) point Additionally the Respiratory Rate time base has now been shortened by the increased Respiratory Rate, though visually it appears identical to the old time base, though the cursor speed of travel would be perceived as increased. This new minimum level safe Tidal Volume and Minute Ventilation would certainly be in a significant hypoventilation range, and failure of the patient to meet this particular stringent minimum level of ventilatory performance would be a dear indication the weaning trial must be immediately halted. By instantly substituting an altered Primary Breathing Pattern breathing prescription in this manner the physician could continue to stress the respiratory muscles to a point of maximal exhaustion, in order to promote muscle rehabilitation and therefore expedite the weaning process, and to immediately terminate the weaning process in order to avoid inappropriate stress and injury to the weakened respiratory muscles. At the same time however, as the visual analog of the breathing pattern appears identical, training and reconditioning of the respiratory center to improved functionality would continue without interruption.

Referring to the simplified schematic diagram in FIG. 6 which is the same basic stand-alone visual biofeedback system, but now additionally working in conjunction with a non-invasive ventilator assistive device. Patient (1) is connected by a Face Mask (21) or Nose Mask (not shown) to Ventilator (7). The ventilator could be a so-called pressure controlled Intermittent Positive Pressure Breathing (IPPB) device, or the commercial BiPap device and similar assistive devices. The Ventilator (7) connects to the patient system via Inspiratory Hose (22) which contains an Exhalation Valve (23) and controls (not shown). Inspiration and Expiration air flow is sensed by Flow Transducer (3) which in turn provides differential pressure to Differential Pressure Transducer (4) which in turn provides electronic flow signals to Computer (5) to be integrated into Tidal Volume data and displayed on CRT Visual Display (6). The Tidal Volume data could also be obtained from an external chest movement sensing device, such as the Respitrace device, without parting from the inventive concept. Typically these ventilator assistive devices sense patient inspiration which triggers Ventilator (7) inspiratory air flow. Typically these ventilatory assistive devices are so-called Pressure Limited devices, which sense a predetermined level of maximum inspiratory pressure by appropriate pressure sensors within the patient Inspiratory Hose (22) circuit(not shown), which in turn then terminates the inspiratory air flow and thus permitting expiration via Exhalation Valve (23). It follows therefore that patient performance is crucial in both initiating ventilator inspiration and well as terminating inspiration to permit exhalation. If the patient efforts are out of synchrony with the ventilator, for example if the patient is trying to breathe out as the ventilator is attempting to deliver an inspiratory breath, there will be premature system pressurization and the ventilator will terminate inspiration before an adequate inspiratory breath has been delivered. Further, if the patient does not exhale completely down to the appropriate Resting Expiratory Level (or Functional Residual Capacity) there will be progressive so-called "air trapping" and the development of an overinflated chest, which in turn will prohibit delivery of the following breaths of fresh gas to the lungs. Proper patient breathing control is therefore crucial, in order to permit proper ventilator action, and particularly so in this type of pressure limited ventilatory assistive device. Proper patient breathing is achieved by visual biofeedback prompting and control from appropriate breathing pattern prescriptions on CRT Visual Display (6).

This invention has been described with computer means as a part of the overall system. The concept may likewise be implemented in a stand-alone device using dedicated microprocessor logic means and dedicated ancillary electronic means, for example, with all electronic components compiled into a single integrated functional electronic chip device. The scope of this invention therefore is not meant to be limited to requiring the use of a general computer or general micro-computer based devices.

This invention has been described with a unique display means whereby the Tidal Volume ordinate axis and Respiratory Rate time abscissa axis are internally calibrated to a full screen display. Alternatively the display could be a standard Volume/Time display or autoscaling displays without departing from the visual biofeedback inventive concepts.

While the invention has been explained by particular examples in the specifications and in the drawing, there is no intent to limit the inventive concept specifically to this description.

What is claimed is:

1. A method for monitoring a respiratory patient to evaluate and train the patient for respiratory ventilator weaning, comprising:

measuring the patient's respiration air volume during a series of spontaneous breathing cycles for establishing patient respiration parameters;

establishing a visual patient inspiration and expiration breathing pattern comprising determined tidal volume, respiratory rate, inspiration to expiration time ratio, end inspiration and end expiration breath hold times, and inspiration and expiration waveforms;

evaluating patient respiration performance data during a further series of spontaneous breathing cycles and comparing said respiration performance to the established visual patient inspiration and expiration breathing patterns;

sensing substantial deviation from the established respiratory pattern by error limits;

providing an actuation signal in response to sensed deviation; and providing ventilator operation for assisted respiration in response to the actuation signal.

2. The method of claim 1 wherein patient data includes tidal volume, inspiration rate and expiration rate at ambient pressure in the absence of ventilator assistance.

3. The method of claim 1 wherein the patient respiration performance data is displayed in real time along with an established breathing pattern;

as a rectilinear coordinate having an abscissa time coordinate containing at least one respiratory cycle and an ordinate tidal volume.

4. A method for monitoring a respiratory ventilator patient having a ventilator operatively connected to a patient respiratory measuring and visual biofeedback system, comprising:

measuring the patient's respiration and establishing patient respiration data, including spontaneous breathing inspiration and expiration patterns;

storing the measured patient respiratory measuring and visual biofeedback system respiration data for retrieval and display;

displaying a prescribed inspiration-expiration pattern for visual feedback and comparison of patient performance under dynamic testing conditions;

evaluating patient performance to determine the patient's ability to breath adequately in the absence of ventilator operation;

sensing substantial patient non-compliance with at least one prescribed respiratory pattern;

sending a signal representative of said non-compliance from the respiratory measuring and visual biofeedback system to actuate alarms or the ventilator for assisting respiration.

5. A method for monitoring a respiratory ventilator patient according to claim 4 further comprising the steps of:

displaying a first prescribed inspiration-expiration pattern during patient compliance, said first pattern prescribing tidal volume adequate for prolonged spontaneous breathing;

displaying a second prescribed inspiration-expiration pattern following at least one level of of patient non-compliance with a minimum tidal volume, said second pattern having a substantially lower tidal volume than said first pattern but appearing visually identical; and actuating ventilator operation in response to patient non-compliance with the second pattern tidal volume.

6. A method for monitoring a respiratory ventilator patient according to claim 4 wherein the patient data is displayed in real time along with an established breathing pattern;

as a rectilinear coordinate having an abscissa time coordinate containing at least one respiratory cycle and an ordinate tidal volume.

7. A method for monitoring a respiratory patient to evaluate the patient for respiratory ventilator weaning, comprising:

providing a respiratory ventilator having an actuator for controlling operation;

measuring the patient's respiration air volume during a series of spontaneous breathing cycles for establishing patient respiration parameters in the absence of ventilator assistance;

displaying a visual patient inspiration and expiration breathing pattern comprising determined tidal volume, respiratory rate, inspiration to expiration time ratio, and inspiration and expiration waveforms;

evaluating patient respiration performance during a further series of spontaneous breathing cycles and comparing said respiration performance to displayed visual patient inspiration and expiration breathing patterns;

sensing substantial deviation from the displayed respiratory pattern; and actuating ventilator operation in response to sensed deviation from the displayed pattern.

8. The method of claim 7 wherein patient data is displayed in real time superimposed with a prescribed breathing pattern as a rectilinear coordinate having an basis time coordinate containing at least one respiratory cycle and an ordinate tidal volume.

9. A method for monitoring a respiratory ventilator patient having a ventilator operatively connected to a patient respiratory measuring and visual biofeedback system, comprising:

measuring the patient's respiration parameters, including spontaneous breathing inspiration and expiration patterns;

storing the measured patient respiratory measuring and visual biofeedback system respiration data for retrieval and display;

displaying a prescribed inspiration-expiration pattern for visual feedback and comparison of patient performance under dynamic testing conditions;

evaluating patient performance to determine the patient's ability to breath adequately in the absence of ventilator operation;

displaying a first prescribed inspiration-expiration pattern during patient compliance;

sensing substantial patient non-compliance with at least one prescribed respiratory pattern; and displaying a second prescribed inspiration-expiration pattern following at least one level of patient non-compliance.

10. A method for monitoring a respiratory ventilator patient according to claim 9 including a step of sending a signal representative of said non-compliance from the respiratory measuring and visual biofeedback system to actuate the ventilator for assisting respiration.

11. A method for monitoring and training patient breathing during weaning from ventilator dependency to assure adequate performance and safety and to provide visual respiratory biofeedback breathing patterns to prompt respiratory muscular function and respiratory center neurologic signals to normal performance, comprising the steps of:

a) setting desired breathing patterns within desired ventilation parameters to establish and monitor a low level of ventilation to define minimum safe levels of ventilation, and to permit definition of patient exhaustion and need to terminate a weaning trial;

b) conducting a consecutive series of weaning trials with unassisted spontaneous breathing, wherein a visual biofeedback monitor is operative during a series of respiratory cycles before sounding an alarm and intervening with ventilator operation; and c) providing a signal for ventilator actuation to assist, when the patient's respiratory performance is outside predetermined safe level of ventilation.

* * * * *

UNITED STATES PATENT AND TRADEMARK OFFICE
CERTIFICATE OF CORRECTION

PATENT NO. : 6,273,088 B1
DATED : August 14, 2001
INVENTOR(S) : Deane Hillsman

Page 1 of 1

It is certified that error appears in the above-identified patent and that said Letters Patent is hereby corrected as shown below:

Column 2,
Line 36, change "dearly" to -- clearly --
Line 39, change "modem" to: -- modern --

Column 3,
Line 13, change "dear" to -- clear --

Column 11,
Line 25, change "dosed" to -- closed --

Signed and Sealed this

Sixth Day of November, 2001

Attest:

NICHOLAS P. GODICI
*Attesting Officer*    *Acting Director of the United States Patent and Trademark Office*